US010260466B2

(12) United States Patent
Beers et al.

(10) Patent No.: US 10,260,466 B2
(45) Date of Patent: Apr. 16, 2019

(54) ULTRASONIC CONTAMINANT DETECTION SYSTEM

(71) Applicants: David F. Beers, Waipahu, HI (US); Michael R. Strong, Warrenton, VA (US); John R. Sevick, Nokesville, VA (US); Michael E. Mullen, Lewisberry, PA (US)

(72) Inventors: David F. Beers, Waipahu, HI (US); Michael R. Strong, Warrenton, VA (US); John R. Sevick, Nokesville, VA (US); Michael E. Mullen, Lewisberry, PA (US)

(73) Assignee: Progeny Systems Corporation, Manassas, VA (US)

(*) Notice: Subject to any disclaimer, the term of this patent is extended or adjusted under 35 U.S.C. 154(b) by 241 days.

(21) Appl. No.: 15/142,953

(22) Filed: Apr. 29, 2016

(65) Prior Publication Data
US 2017/0315098 A1    Nov. 2, 2017

(51) Int. Cl.
*G01N 29/42* (2006.01)
*G01N 29/24* (2006.01)
(Continued)

(52) U.S. Cl.
CPC ............ *F02M 37/22* (2013.01); *G01N 15/06* (2013.01); *G01N 15/10* (2013.01); *G01N 29/028* (2013.01);
(Continued)

(58) Field of Classification Search
CPC .. G01N 29/02; G01N 29/2437; G01N 29/032; G01N 29/2456; G01N 29/222;
(Continued)

(56) References Cited

U.S. PATENT DOCUMENTS 3,208,286 A * 9/1965 Richard ................. G01N 15/02
367/87
3,648,513 A    3/1972 Patterson
(Continued)

FOREIGN PATENT DOCUMENTS

EP    2246698    11/2010

OTHER PUBLICATIONS

Nemarich et al., On-Line Wear Particle Monitoring Based on Ultrasonic Detection and Discrimination, Research and Development Report, May 1989, PAS-89-7, David Taylor Research Center, Bethesda, MD.
(Continued)

*Primary Examiner* — Lisa M Caputo
*Assistant Examiner* — Rose M Miller
(74) *Attorney, Agent, or Firm* — Law Office of Steven R. Olsen, PLLC; Steven R. Olsen

(57) ABSTRACT

The invention generally provides a system and method for detecting, measuring, and/or classifying particulate and/or water contaminants in a fluid supply line, storage tank, or sump. Embodiments of the invention provide a contaminant detection apparatus with a detection chamber and a detection module. The detection chamber includes a housing with an internal fluid conduit and one or more acoustic transducers disposed in the housing. Alarms and/or automatic signaling may be included to shut off valves or pumps when contaminants are detected.

6 Claims, 10 Drawing Sheets

(51) Int. Cl.
*G01N 29/44* (2006.01)
*F02M 37/22* (2019.01)
*G01N 15/10* (2006.01)
*G01N 29/028* (2006.01)
*G01N 29/22* (2006.01)
*G01N 29/34* (2006.01)
*G01N 15/06* (2006.01)
*G01N 33/28* (2006.01)
*G01N 15/00* (2006.01)

(52) U.S. Cl.
CPC ......... *G01N 29/221* (2013.01); *G01N 29/222* (2013.01); *G01N 29/2437* (2013.01); *G01N 29/343* (2013.01); *G01N 29/345* (2013.01); *G01N 29/42* (2013.01); *G01N 29/4445* (2013.01); *G01N 33/2847* (2013.01); *G01N 33/2888* (2013.01); *G01N 2015/003* (2013.01); *G01N 2015/0053* (2013.01); *G01N 2291/02416* (2013.01)

(58) Field of Classification Search
CPC ............... G01N 29/343; G01N 29/348; G01N 2291/02416; G01N 2291/106; G01N 15/10; F02M 37/22; H04B 1/16
USPC .......... 73/570, 599, 600, 602, 627, 628, 646
See application file for complete search history.

(56) References Cited

U.S. PATENT DOCUMENTS

| | | | |
|---|---|---|---|
| 3,791,200 A | | 2/1974 | Hayre |
| 4,050,055 A | | 9/1977 | DiLeo |
| 4,080,837 A | | 3/1978 | Alexander et al. |
| 4,112,735 A | * | 9/1978 | McKnight .............. G01N 29/02 73/19.03 |
| 4,214,484 A | | 7/1980 | Abts |
| 4,217,781 A | | 8/1980 | Abts |
| 4,339,944 A | | 7/1982 | Abts et al. |
| 4,365,515 A | * | 12/1982 | Abts .................... G01N 29/032 310/334 |
| 4,376,255 A | | 3/1983 | Kleinschmidt |
| 4,527,420 A | * | 7/1985 | Foote .................... G01N 15/02 73/61.75 |
| 4,542,644 A | * | 9/1985 | Claytor ................... G01F 1/663 73/599 |
| 4,580,444 A | * | 4/1986 | Abts .................... E21B 47/101 73/599 |
| 4,607,520 A | * | 8/1986 | Dam .................... G01N 29/032 73/19.03 |
| 4,656,869 A | | 4/1987 | Zacharias |
| 4,739,662 A | * | 4/1988 | Foote ................... G01N 29/032 73/599 |
| 5,255,564 A | | 10/1993 | Glad et al. |
| 5,291,773 A | * | 3/1994 | Kamon ................ G01N 29/032 73/24.03 |
| 5,473,934 A | | 12/1995 | Cobb |
| 5,606,130 A | | 2/1997 | Sinha et al. |
| 5,932,806 A | | 8/1999 | Rose et al. |
| 6,013,032 A | | 1/2000 | Savord |
| 6,401,538 B1 | | 6/2002 | Han et al. |
| 6,959,601 B2 | | 11/2005 | Sinha |
| 7,480,603 B1 | | 1/2009 | San et al. |
| 8,286,466 B2 | | 10/2012 | Gysling |
| 2003/0018260 A1 | | 1/2003 | Erikson |
| 2003/0139687 A1 | | 7/2003 | Abreu |
| 2003/0150262 A1 | | 8/2003 | Han et al. |
| 2004/0000841 A1 | | 1/2004 | Phelps et al. |
| 2004/0002656 A1 | | 1/2004 | Sheljaskow et al. |
| 2004/0197922 A1 | | 10/2004 | Cooper |
| 2005/0109112 A1 | | 5/2005 | Gysling et al. |
| 2005/0172737 A1 | | 8/2005 | Bond |
| 2006/0156820 A1 | | 7/2006 | Jones et al. |
| 2007/0232910 A1 | | 10/2007 | Hwang et al. |
| 2009/0126481 A1 | | 5/2009 | Burris |
| 2009/0272190 A1 | | 11/2009 | Hofmann |
| 2010/0141460 A1 | | 6/2010 | Tokhtuev |
| 2013/0167622 A1 | | 7/2013 | Frivik |
| 2015/0226595 A1 | | 8/2015 | Reimer et al. |
| 2016/0003783 A1 | * | 1/2016 | Nara .................... G01N 29/043 73/632 |
| 2016/0077198 A1 | | 3/2016 | Leone et al. |

OTHER PUBLICATIONS

Liu et al., Ultrasonic Determination of Water Concentration in Ethanol Fuel Using Artificial Neural Networks, Transactions of the ASABE, 2012, pp. 1865-1872, vol. 55(5), American Society of Agricultural and Biological Engineers.

Hella KGaA Hueck & Co., Hella Sensors Continuously Monitor Engine Oil Level, Quality, Oct. 8, 2008, Business Wire, available at www.businesswire.com/news.

* cited by examiner

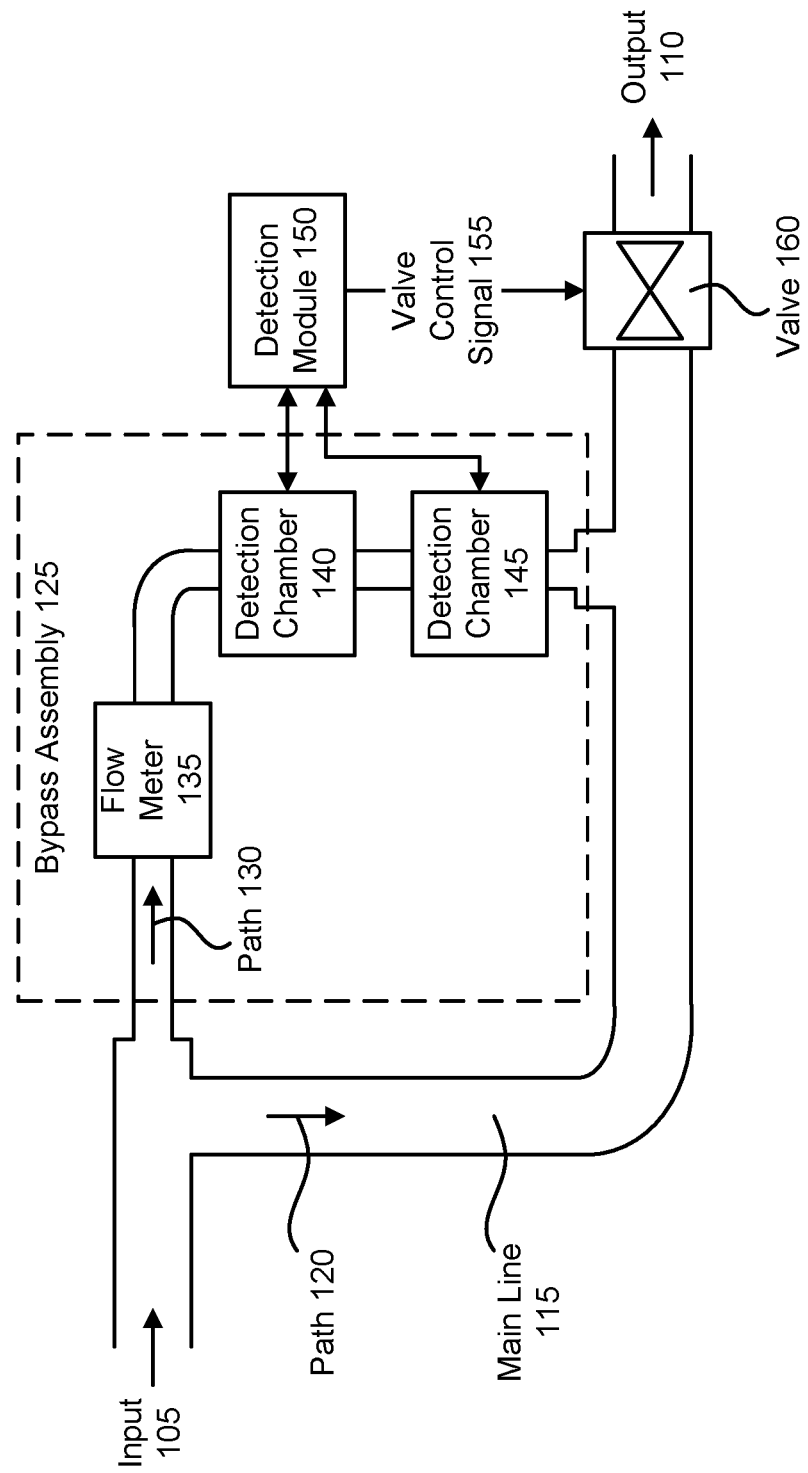

ULTRASONIC CONTAMINANT DETECTION SYSTEM

STATEMENT REGARDING FEDERALLY SPONSORED RESEARCH OR DEVELOPMENT

This invention was made with government support under SBIR contract nos. W911W611C0019 and W56HZV12C0268 awarded by the U.S. Dept. of Defense. The government has certain rights in the invention.

BACKGROUND

Field of Invention

The invention relates generally to a system and/or method for detecting contaminants in a fluid stream. More specifically, but not by way of limitation, embodiments of the invention utilize multiple ultrasonic transducers in a system that is configured to perform an improved detection and classification method for contaminants in a fluid supply line, tank, or sump.

Description of the Related Art

Contamination in the form of particulates and/or water can interrupt fuel or oil flow in engines, damage bearings, and lead to catastrophic failure. Typical risk mitigation techniques include in-line filtering to trap particulates during fueling and/or off-line batch testing of fuel or oil to detect particulates and/or water content. Such conventional systems and methods for managing contamination have many shortcomings, however. For example, in-line particulate filters require maintenance and are subject to failure. Moreover, off-line batch testing of fuel or oil in storage, delivery, and recirculation systems may be ill-timed with respect to contamination events. A need exists for a reliable system that can detect, classify, and measure contamination in fluid storage and delivery systems in near real time.

SUMMARY OF THE INVENTION

The invention seeks to overcome one or more of the limitations described above by providing an improved system and method for detecting, measuring, and classifying particulate and/or water in a fluid supply line, storage tank, or sump. Embodiments of the disclosed system include local or remote alarms and/or automatic signaling to shut off valves or pumps when contaminants are detected.

Embodiments of the invention provide a contaminant detection apparatus with a detection chamber. The detection chamber includes a housing with an internal fluid conduit and one or more acoustic transducers disposed in the housing. Embodiments also include a detection module coupled to the one or more transducers. The detection module is configured to perform one or more processes to detect contaminants in a fluid disposed in the internal fluid conduit, determine the composition of the contaminants, determine a concentration of the contaminants, and/or resolve the size of particulate contaminants.

BRIEF DESCRIPTION OF THE DRAWINGS

Embodiments of the invention are described with reference to the following drawings, wherein:

FIG. 8-1 is an illustration of a first contaminant detection histogram, according to an embodiment of the invention;

FIG. 8-2 is an illustration of a second contaminant detection histogram, according to an embodiment of the invention;

DETAILED DESCRIPTION

Figure 2:
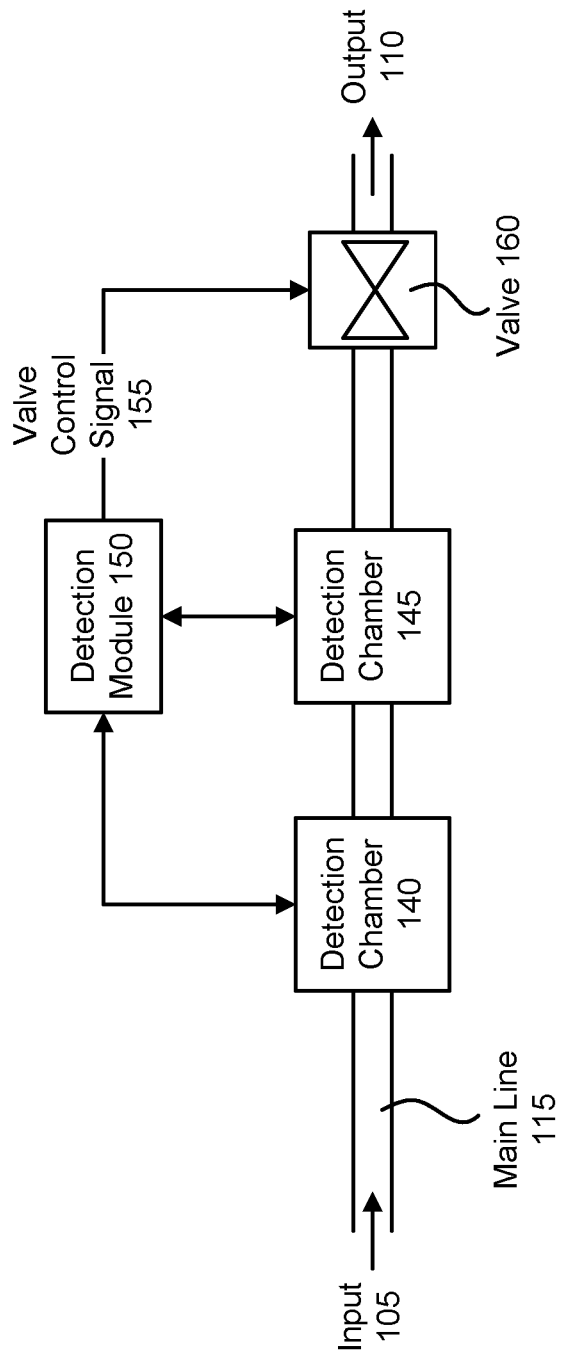
FIG. 2 is a schematic diagram of a fuel delivery system, according to an embodiment of the invention.

Embodiments of the invention are described with reference to FIGS. 1-11. Such embodiments are meant to be illustrative and not restrictive. Reference designators are reused for the same or similar features. Features in the figures are not necessarily drawn to scale. Some features illustrated in the drawings may be exaggerated in scale. Other features may be simplified or omitted for descriptive clarity.

Fuel Delivery System

Figures 1, 8:
FIG. 1 is a schematic diagram of a fuel delivery system, according to an embodiment of the invention.
FIG. 8 is a detailed flow diagram of a particulate size classification method, according to an embodiment of the invention.
Figures 2, 8:
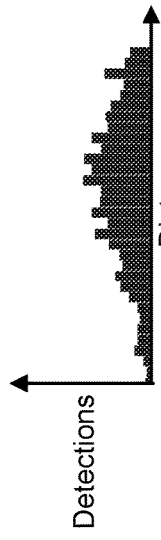
Figure 8:
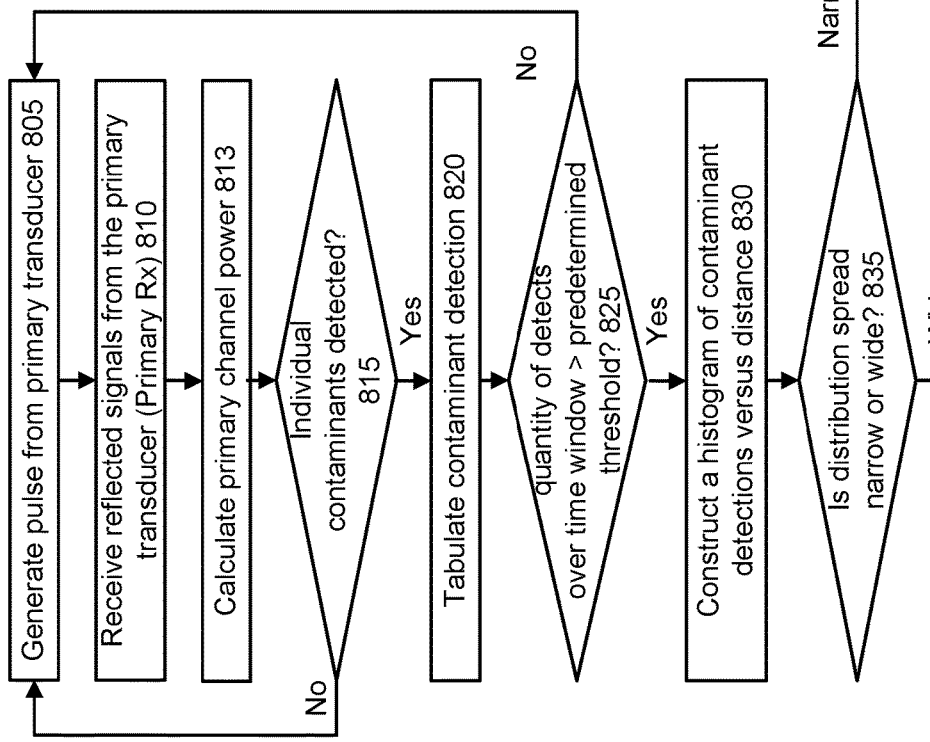

FIG. 1 is a schematic diagram of a fuel delivery system, according to an embodiment of the invention. As shown therein, the fuel delivery system is configured to transport fuel from an input port 105 to an output port 110. A main line 115 carries a first portion of fuel via path 120. A bypass assembly 125 carries a second portion of fuel via path 130. In the illustrated embodiment, the bypass assembly 125 includes a flow meter 135, a first detection chamber 140, and a second detection chamber 145, all coupled in series. As an example, the first detection chamber 140 could be configured for coarse sensitivity for the detection of relatively large particles, and the second detection chamber 145 could be configured for fine sensitivity the detection of relatively small particles. A detection module 150 is coupled to the first and second detection chambers 140, 145. A valve 160 is disposed in the main line 115 prior to the output port 110 but after discharge from the bypass assembly 125. The detection module 150 is coupled to the valve 160 to provide a valve control signal 155.

An embodiment of the detection chambers 140, 145 is described below with reference to FIG. 3. An embodiment of the detection module 150 is described below with reference to FIGS. 4-9.

In operation, fuel received at the input port 105 is divided, not necessarily equally, between the first path 120 and the second path 130. Fuel in the second path 130 passes through the first and second test chambers 140, 145. The detection module 150 sends acoustic signals to the first and second test chambers 140, 145 and receives reflected acoustic signals from the first and second test chambers 140, 145. The detection module 150 detects, classifies, and/or measures contaminants in the fuel flowing through path 130 based on the reflected acoustic signals. When the concentration of contamination in the fuel exceeds predetermined thresholds, the detection module 150 outputs the valve control signal 155 to close the valve 160 and prevent the flow of fuel at the output port 110.

Variations in the delivery system illustrated in FIG. 1 and described above are possible. For example, such a system or variant thereof may be used for delivery of a fluid other than fuel. In an alternative embodiment, the main line 115 could include a regulation valve to achieve a desired flow rate in the bypass assembly 125, for instance as measured by the flow meter 135. In other applications, the flow meter 135 may not be required. Depending upon detection requirements, a single test chamber may be sufficient in the bypass assembly 125. Conversely, three or more test chambers could be used, according to design choice. In embodiments of the invention, the detection module 150 could output an alarm signal instead of, or in combination with, the valve control signal 155. The detection module 150 could be configured to output a control signal to turn-off a pump in a fluid delivery or recirculation system. Other system alternatives are discussed below with reference to FIGS. 2, 10, and 11.

FIG. 2 is a schematic diagram of a fuel delivery system, according to an embodiment of the invention. As shown, the detection chambers 140, 145 and the valve 160 may be connected in series along the main line 115. The detection module 150 is coupled to the first and second detection chambers 140, 145 and to the valve 160. In operation, fuel received at the input port 105 passes through the first and second detection chambers 140, 145. The detection module 150 sends acoustic signals to the first and second detection chambers 140, 145 and receives reflected acoustic signals from the first and second detection chambers 140, 145. The detection module 150 then detects, classifies, and/or measures contaminants in the fuel based on the reflected acoustic signals. When the concentration of contamination in the fuel exceeds predetermined thresholds, the detection module 150 outputs the valve control signal 155 to close the valve 160 and prevent the flow of fuel at the output port 110.

Variations in the delivery system illustrated in FIG. 2 and described above are possible. For example, such a system or variant thereof may be used for delivery of a fluid other than fuel. Depending upon detection requirements, a single detection chamber may be sufficient in the main line 115. Conversely, three or more detection chambers could be used, according to design choice. In embodiments of the invention, the detection module 150 could output an alarm signal instead of, or in combination with, the valve control signal 155. In other embodiments, the detection module 150 could be configured to output a control signal to turn-off a pump in a fluid delivery or recirculation system.

Detection Chamber

Figure 3:
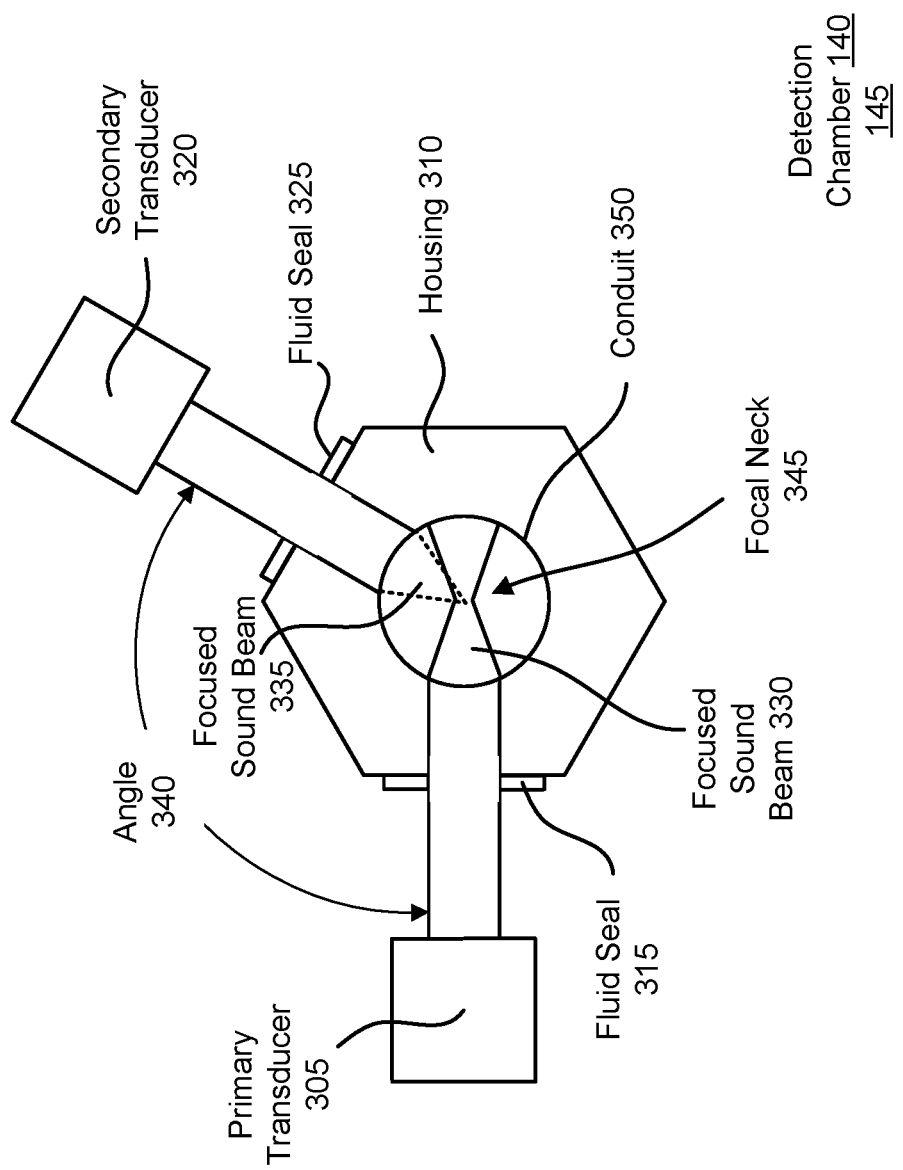
FIG. 3 is a sectional view of a detection chamber, according to an embodiment of the invention.

FIG. 3 is a sectional view of a detection chamber, according to an embodiment of the invention. The detection chamber illustrated in FIG. 3 could be representative of detection chamber 140 or 145. In the illustrated embodiment, a primary transducer 305 and a secondary transducer 320 are disposed a housing 310 at an angle 340 with respect to each other. The primary and secondary transducers 305, 320, may each be an ultrasonic piezoelectric transducer and may be configured, for example, to operate at a frequency somewhere in the 10-25 MHz range, according to application needs. The resolution of each detection chamber 140, 145, is a function of the frequency of operation of the transducers 305, 320. For example, testing has shown that two 10 MHz transducers can resolve particulate contaminants that are less than 10 microns in size. The secondary transducer 320 is disposed in the housing 310 to receive side-scattered energy (as further described below). The angle 340 is 120 degrees in the illustrated embodiment, as defined by the outer contour of the housing 310. Fluid seals 315, 325 are disposed at the interface of the housing 310 and the transducers 305, 320, respectively, to prevent leakage of fuel or other fluid from inside conduit 350.

In operation, fuel or other fluid flows in the conduit 350. In response to an electrical pulse stream, the primary transducer 305 outputs a stream of acoustic pulses at focused sound beam (focal beam) 330 having a focal neck 345. The stream of acoustic pulses may be, for instance, a 125 nanosecond square wave with a pulse repetition rate of 1000 pulses/second and a 15 second duration. Contaminants in the fuel or other fluid cause reflected acoustic signals. A first portion of such reflected acoustic signals is received by the primary transducer 305 from the focused sound beam 330. A second portion of the reflected acoustic signals is received by the secondary transducer 320 from focused sound beam (focal beam) 335 at the focal neck 345. The primary and secondary transducers 305, 320 convert their respective received acoustic signals into electrical signals.

Variations to the configuration illustrated in FIG. 3 and described above are possible. For instance, for some applications, a secondary transducer 320 may not be required. Higher-frequency transducers 305, 320 (compared to what is described above) could be used to detect smaller particle sizes. Embodiments having multiple detectors with transducers of differing frequencies can allow selectable low-pass, band pass, or high pass filtering depending upon particle size of interest. Moreover, an unfocused transducer with a cylindrical beam could be used in place of the primary transducer 305 and/or the secondary transducer 320. The angle 340 between the primary transducer 305 and the secondary transducer 320 need not be 120 degrees. In general, angle 340 could be anywhere between 0 and 180 degrees (exclusive of 0 and 180 degrees). In an alternative embodiment, the focused sound beam 335 from the secondary transducer 320 crosses the focused sound beam 330 inside (rather than at) the focal neck 345. The stream of acoustic pulses output from the primary transducer 305 could vary from what is described above. For instance, the stream of acoustic pulses from the primary transducer 305 could employ an alternative waveform, pulse repetition rate, or duration compared to what is described above. The outer contour of the housing 310 need not have a hexagonal cross-section. In addition, alternative sealing approaches can be used in place of the fluid seals 315, 325.

Detection Module

Figure 4:
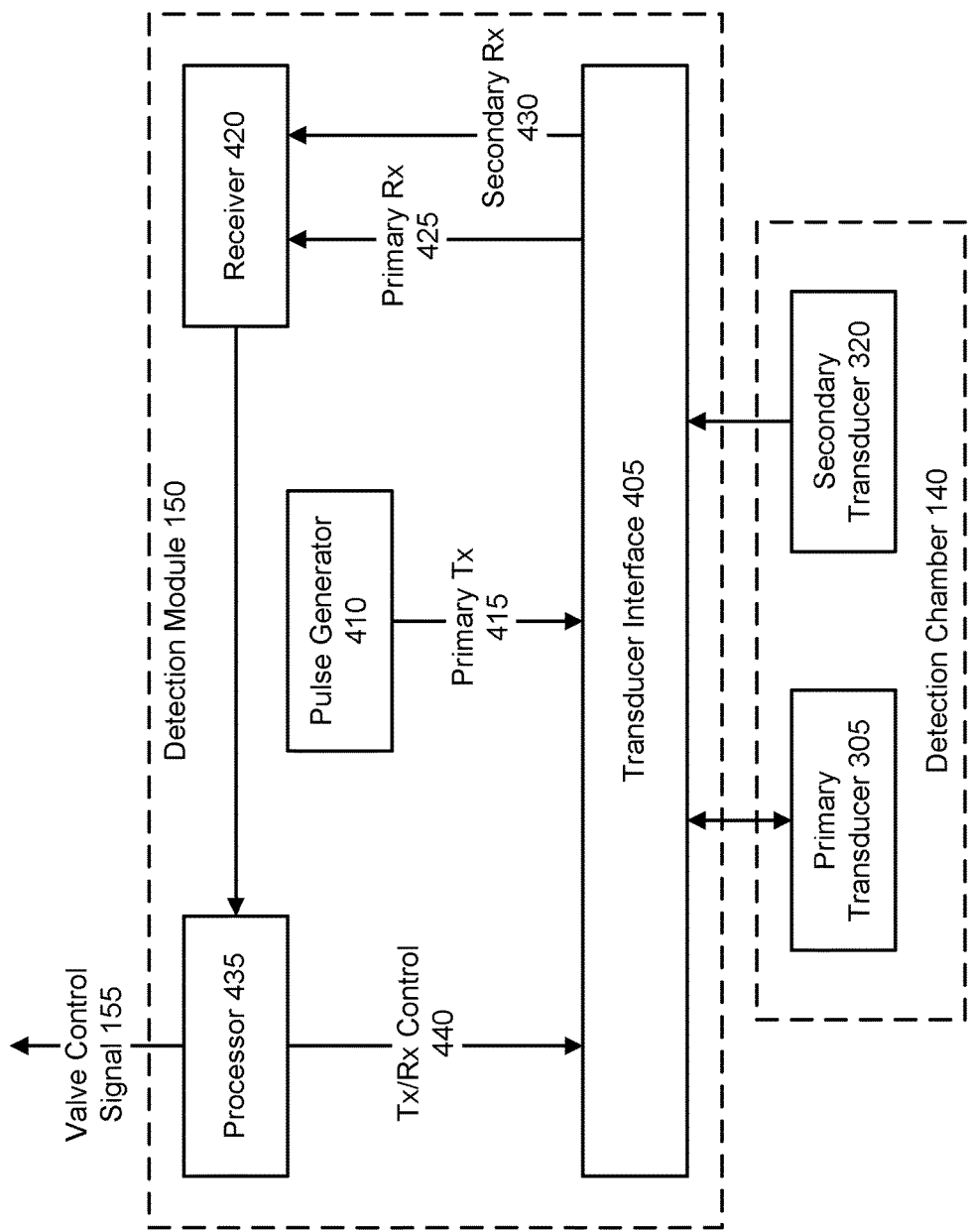
FIG. 4 is a functional block diagram of a detection module and a detection chamber, according to an embodiment of the invention.

FIG. 4 is a functional block diagram of a detection module and a detection chamber, according to an embodiment of the invention. As shown therein, a detection module 150 is coupled to a single detection chamber 140. As described above, the detection chamber 140 may include a primary transducer 305 (to transmit acoustic signals and receive reflected acoustic signals) and a secondary transducer 320 (to receive reflected acoustic signals only). In the illustrated embodiment, the detection module 150 includes a transducer interface 405 that is coupled to a pulse generator 410, receiver 420 and processor 435. The receiver 420 and processor 435 are also coupled to each other. Power supply features are omitted for clarity.

An embodiment of the transducer interface 405 is described with reference to FIG. 5 below. The pulse generator 410 can be or include, for instance, a software-defined radio (SDR) configured to output an analog pulse stream where each pulse has a width of 125 nanoseconds. The receiver 420 preferably includes analog-to-digital converters (ADC's) to convert the Primary RX signal 425 and Secondary Rx signal 430 to digital data. In embodiments of the invention, the receiver 420 may also be configured to filter the digital data. The processor 435 is preferably a digital processor. For example, the processor 435 may be or include a microcomputer, a digital application-specific integrated circuit (ASIC) or a field-programmable gate array (FPGA).

In operation, the pulse generator 410 outputs Primary Tx signal 415 (an electrical transmit signal that is preferably a pulse stream) to the transducer interface 405. The transducer interface 405 selectively couples the Primary TX signal 415 to the primary transducer 305 based on Tx/Rx Control signal 440 (a transmit/receive control signal output from the processor 435). The transducer interface 405 receives a reflected signal from the primary transducer 305, converts said signal to a Primary Rx signal 425, and outputs the Primary Rx signal 425 to the receiver 420. Likewise, the transducer interface 405 also receives a reflected signal from the secondary transducer 320, converts said signal to a Secondary Rx signal 430, and outputs the Secondary Rx signal 430 to the receiver 420. The receiver 420 may convert the received signals to digital data and then filter the digital data before outputting the digital data to the processor 435. The processor 435 is preferably configured to output the valve control signal 155 and/or an alarm signal (not shown) when it determines that a contaminant concentration in the fuel or other fluid exceeds a predetermined concentration and/or particulate size threshold. The operation of detection module 150, including certain functions of the processor 435, is discussed below with reference to an exemplary embodiments illustrated in FIGS. 6-9.

Figure 5:
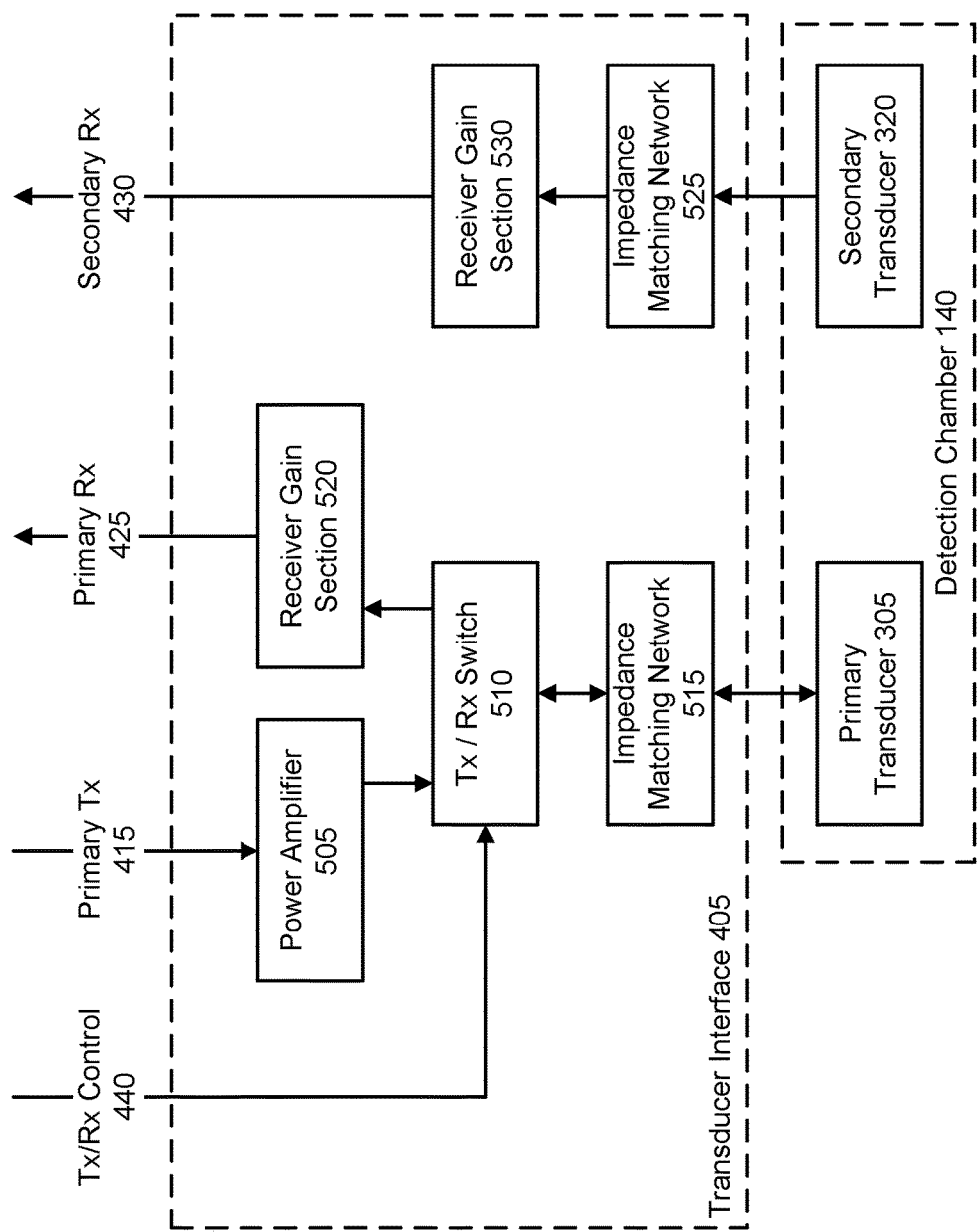
FIG. 5 is a functional block diagram of a transducer interface and a detection chamber, according to an embodiment of the invention.

FIG. 5 is a functional block diagram of a transducer interface and a detection chamber, according to an embodiment of the invention. As shown therein, the transducer interface 405 of a detection module 150 is coupled to a single detection chamber 140. As described above, the detection chamber 140 may include a primary transducer 305 (to transmit acoustic signals and receive reflected acoustic signals) and a secondary transducer 320 (to receive reflected acoustic signals only). In the illustrated embodiment, the transducer interface 405 includes Tx/Rx (transmit/receive) switch 510 that is coupled to a power amplifier 505, an impedance matching network 515, and a receiver gain section 520. The impedance matching network 515 is connected to the primary transducer 305. The transducer interface 405 also includes an impedance matching network 525 and a receiver gain section 530, the impedance matching network 525 being coupled between the secondary transducer 320 and the receiver gain section 530. Power supply features are omitted for clarity.

In operation, the power amplifier 505 amplifies the Primary Tx signal 415. The Tx/Rx control signal 440 configures the transducer interface 405 to operate the primary transducer 305 in either a transmit mode or a receive mode. In the transmit mode, the Tx/Rx switch 510 passes the amplified Primary Tx signal to the primary transducer 305 via the impedance matching network 515. In the receive mode, the Tx/Rx switch 510 passes a reflected (Primary Rx) signal received from the primary transducer 305 (via the impedance matching network 515) to the receiver gain section 520. A reflected (Secondary Rx) signal from the secondary transducer 320 is passed to the receiver gain section 530 via the impedance matching network 525.

Variations of the configuration illustrated in FIG. 5 are possible. For instance, where the pulse generator 410 is configured to output a Primary Tx signal 415 with suitable amplitude for the primary transducer 305, the power amplifier 505 may not be required. Likewise, depending upon design choices with regard to the primary and secondary transducers 305, 320 and the receiver 420, receiver gain sections 520 and/or 530 may not be required. As used herein, the Primary Tx signal may refer to the electrical signal output from the pulse generator 410, or the amplified signal output from the power amplifier 505. The Primary Rx signal may refer to the electrical signal output from the primary transducer 305, the amplified signal output from the receiver gain section 520, or a signal derived from the primary transducer 305 that is output from the receiver 420 to the processor 435. Likewise, the Secondary Rx signal may refer to the electrical signal output from the secondary transducer 320, the amplified signal output from the receiver gain section 530, or a signal derived from the secondary transducer 320 that is output from the receiver 420 to the processor 435.

Figure 6:
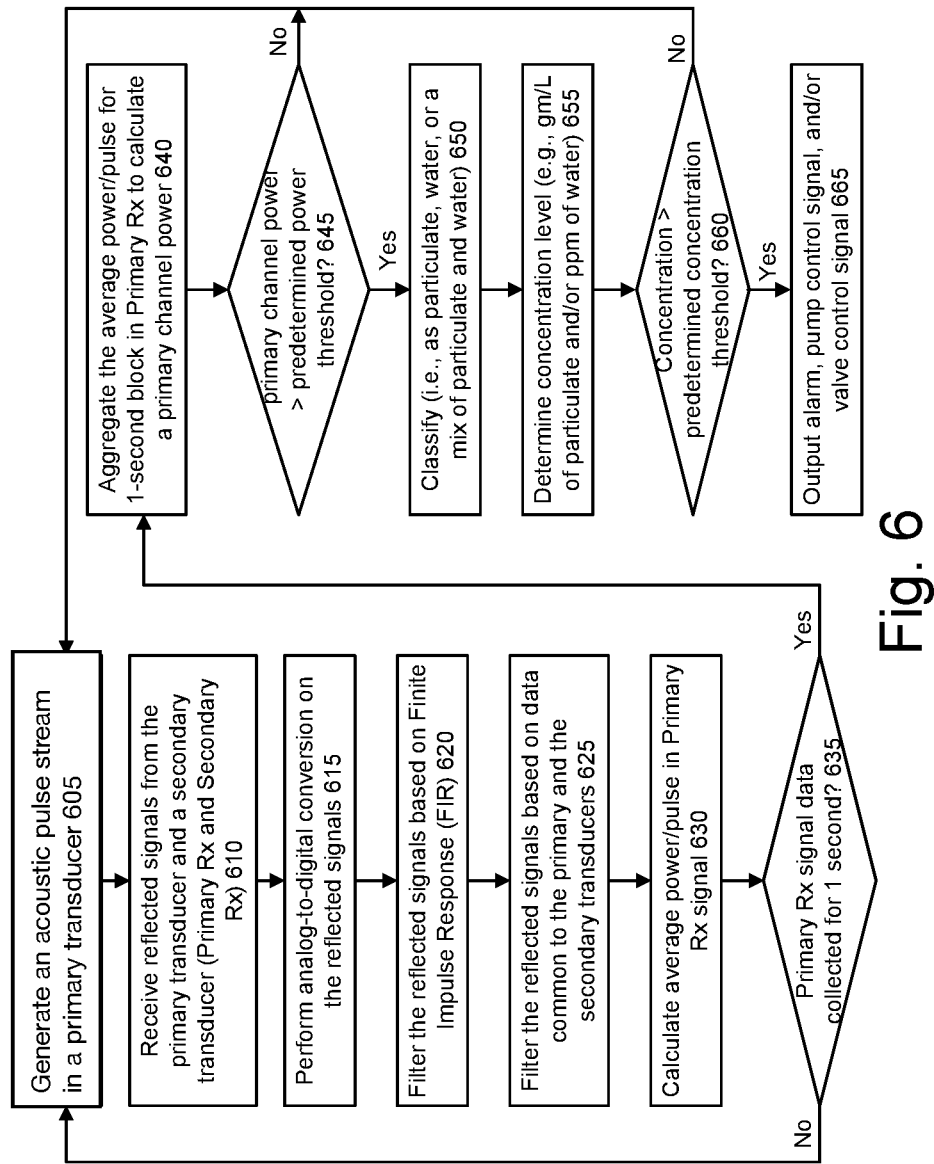
FIG. 6 is a flow diagram of a detection, type classification, and measurement method, according to an embodiment of the invention.

FIG. 6 is a flow diagram of a detection, type classification, and measurement method, according to an embodiment of the invention. The method could be implemented, for instance, using the above-described detection chamber 140 and detection module 150. The illustrated process begins in step 605 by generating an acoustic pulse stream in a primary transducer. The acoustic pulse stream output from the primary transducer may be in response to a primary transmission (Primary Tx) signal. In step 610, the process receives reflected signals from both the primary transducer and a secondary transducer (the Primary Rx and Secondary Rx signals, respectively). Next, in step 615, the process performs an analog-to-digital (A/D) conversion on the reflected signals. The process then filters the reflected signals based on Finite Impulse Response (FIR) in step 620, and further filters the reflected signals to eliminate data common to the primary and the secondary transducers (i.e., a common noise component) in step 625. In step 630, the process calculates an average power/pulse in the Primary Rx signal. The process determines whether Primary Rx signal data has been collected for 1 second in conditional step 635.

Where conditional step 635 is not satisfied, the process returns to step 605; otherwise, the process calculates a primary channel power in step 640 by aggregating the average power/pulse in the Primary Rx signal for a 1-second block. Next, the process determines whether the primary channel power is greater than a predetermined power threshold in conditional step 645.

Where the condition in step 645 is not satisfied, no (or insufficient) contaminants have been detected and the process returns to step 605; otherwise, the process classifies the contaminants according to composition (e.g., as particulate, water, or a mix of particulate and water) in step 650, and then determines a concentration level of particulate and/or water in step 655. An embodiment of classification step 650 and determination step 655 is discussed below with reference to FIG. 7. The process then determines whether the concentration exceeds a predetermined concentration threshold that is based on application requirements in conditional step 660. Step 660 could be based, for example, on the discrete 1-second processing described above or on a moving average.

Where conditional step 660 is not satisfied, the process returns to step 605; otherwise, the process terminates by outputting an alarm, pump control signal, and/or valve control signal in step 665.

Variations to the process illustrated in FIG. 6 and described above are possible. For instance, where the primary and secondary transducers provide a digital output, conversion step 615 is not required. Moreover, the sequence of A/D conversion step 615 and filtering steps 620, 625 could be varied according to design choice, for instance where analog filtering methods are used. A predetermined window of time other than 1 second, or a moving average, could be used in steps 635-640 to calculate the primary channel power, for instance to enhance a signal-to-noise ratio (SNR). In some applications, step 665 could include data logging instead of, or in addition to, alarming and/or control signaling. The process illustrated in FIG. 6 could also be adapted for intermittent (rather than continuous) sampling, e.g. with an operational duty cycle of 1 second per minute.

Figure 7:
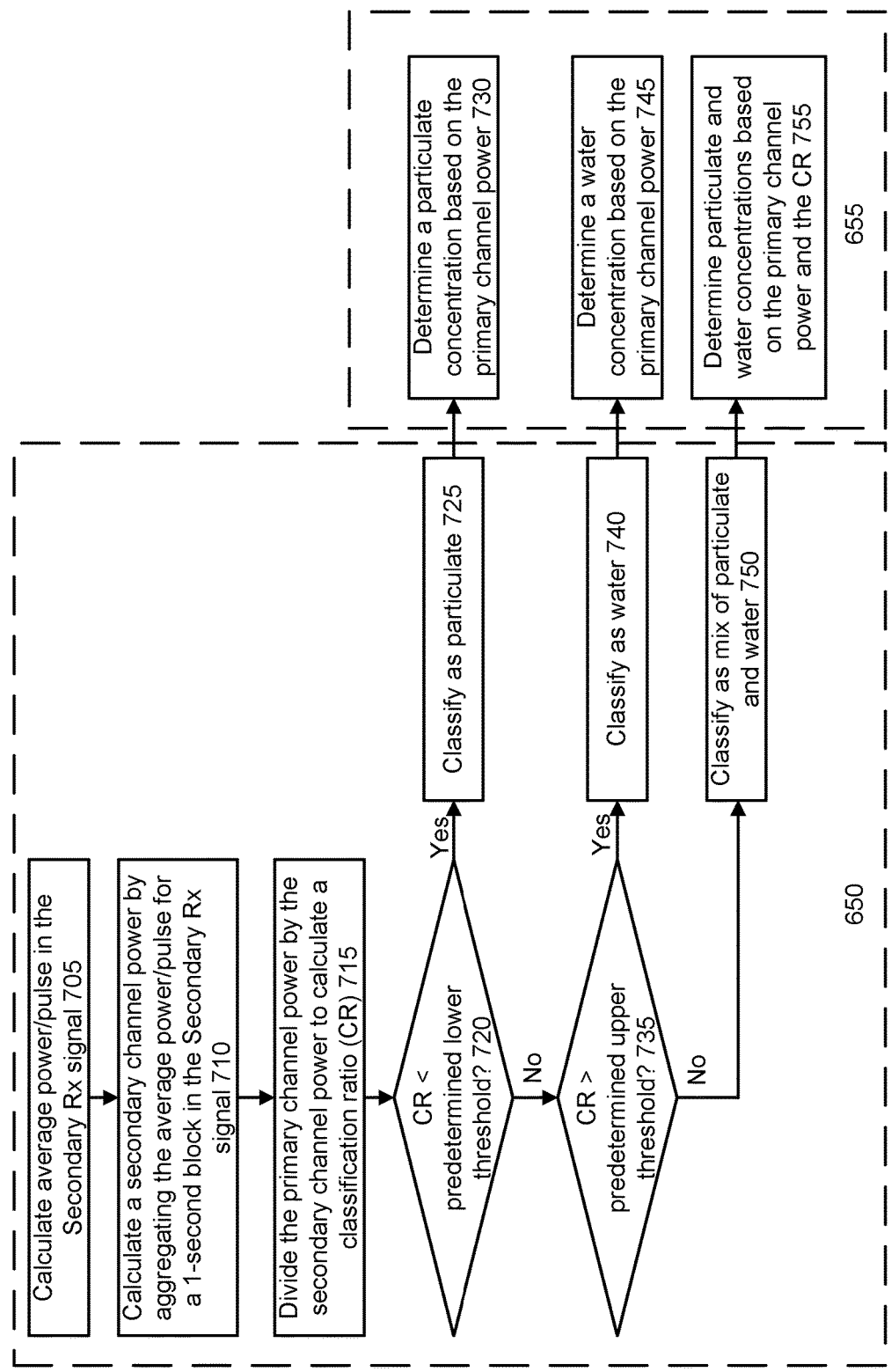
FIG. 7 is a detailed flow diagram of the type classification and determination steps (650 and 655) in FIG. 6, according to an embodiment of the invention.

FIG. 7 is a detailed flow diagram of the type classification and determination steps (650 and 655) in FIG. 6, according to an embodiment of the invention. The process begins by calculating an average power/pulse in the Secondary Rx signal in step 705, and then calculating a secondary channel power by aggregating the average power/pulse in the Secondary Rx signal for 1 second. In alternative embodiments, a window of time other than 1 second, or a moving average power, could be used to calculate the secondary channel power in step 710. In step 715, the process divides the primary channel power by the secondary channel power to calculate a Classification Ratio (CR).

The process then determines whether the CR is less than a predetermined lower threshold in conditional step 720. If conditional step 720 is satisfied, the process classifies the contaminant as being particulate in step 725 and then determines a particulate concentration based on the primary channel power in step 730; otherwise, the process advances to conditional step 735 to determine whether the CR is greater than a predetermined upper threshold. If conditional step 735 is satisfied, the process classifies the contaminant as water in step 740 and then determines a water concentration based on the primary channel power in step 745; otherwise, the process classifies the contaminant as a mix of particulate and water in step 750 and then determines particulate and water concentrations based on the primary channel power and the CR in step 755. Determination steps 730, 745, and 755 may be performed using lookup tables or matrices that are populated with data from empirical testing. For instance, steps 730 and 745 may each use a simple input/output table that is a function of primary channel power. The table used in step 730 is populated with data from test conditions involving pure particulate contamination; the table used in step 745 is populated with data from test conditions involving pure water contamination. The data used in step 755 may be placed in a matrix since the effect is a function of both the primary channel power and the CR. In embodiments of the invention, a single matrix contains all data used in determination steps 730, 745, and 755.

As an example of the embodiment of step 650 illustrated in FIG. 7 and described above, in tests involving a variety of known contaminants in a fuel, a laboratory implementation of the detection module 150: reliably predicted particulate contamination where CR was less than a lower threshold of 5.4; reliably predicted water contamination where CR was above an upper threshold of 6.1; and reliably predicted a mix of particulate and water contamination, with the relative concentrations of each, for all other CR values.

Figure 9:
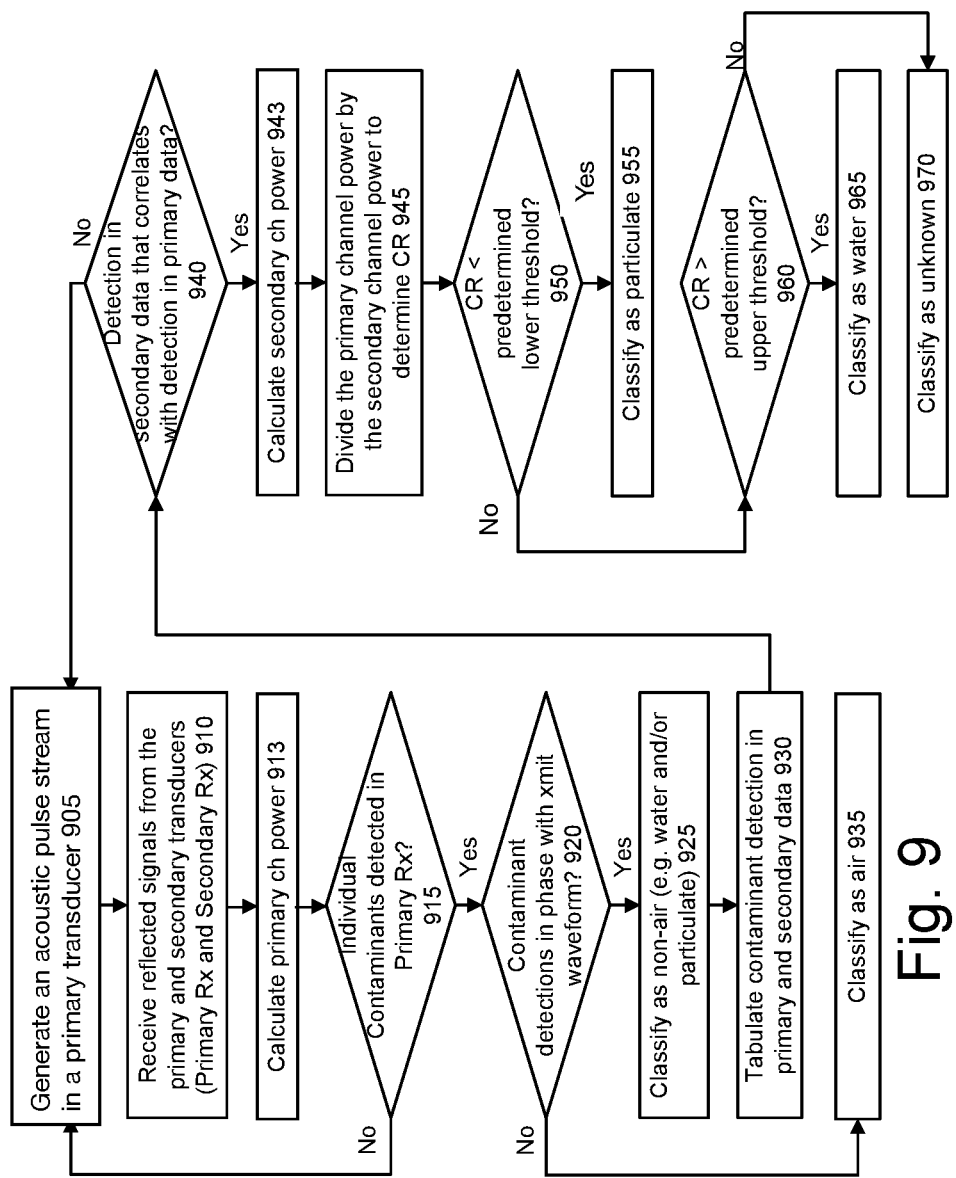
FIG. 9 is a flow diagram of a contaminant type classification method, according to an embodiment of the invention.

FIGS. 8 and 9 illustrate two additional processes that could be performed using the above-described detection chamber 140 and detection module 150.

FIG. 8 is a detailed flow diagram of a particulate size classification method, according to an embodiment of the invention. Advantageously, the method illustrated in FIG. 8 only requires a primary transducer 305 that is configured to generate the focused sound beam 330 (for instance in a detection chamber 140) and a detection module 150. The illustrated process begins in step 805 by generating a pulse signal in a primary transducer. The generated pulse signal may be in response to a primary transmission signal Primary Tx. In step 810, the process receives a reflected signal from the primary transducer (the Primary Rx signal). The process calculates a primary channel power in step 813. Step 813 could include, for instance, calculating an average power/pulse in the Primary Rx signal and then aggregating the average power/pulse over a predetermined period of time. Then, in conditional step 815, the process determines whether individual contaminants are detected. Step 815 is based on the Primary Rx signal and may include comparing the primary channel power to a predetermined threshold.

If the process does not detect contaminants, the process returns to step 805; otherwise the process tabulates contaminant detections in step 820. Tabulation step 820 includes logging the pulse number, measured power, and distance (and/or corresponding time-of-flight) for each pulse of the Primary Rx signal. In conditional step 825, the process determines whether a quantity of defects (contaminant detections) over a predetermined time window exceeds a predetermined threshold. If not, the process returns to step 805; otherwise, the process constructs a histogram of contaminant detections vs. distance (or corresponding time-of-flight of the acoustic signal) in step 830. Then, in conditional step 835, the process determines whether a distribution spread of the resulting histogram is relatively narrow or relatively wide. The primary transducer 305 will have its best resolution in the focal neck 345 (due to maximum power densities). Thus, where the spread is relatively narrow, the process concludes the detected contaminant sizes are at or below the resolution limit of the primary transducer in step 840; otherwise, the process concludes the detected contaminant sizes exceed the transducer resolution limit in step 845.

FIG. 8-1 is an illustration of a first contaminant detection histogram, according to an embodiment of the invention. FIG. 8-2 is an illustration of a second contaminant detection histogram, according to an embodiment of the invention. FIG. 8-1 is representative of a histogram that is determined in step 835 to be relatively narrow; FIG. 8-2 is representative of a histogram that is determined in step 835 to be relatively wide. As an example, in the case of a primary transducer operating at 10 MHz, a contaminant detection histogram constructed in step 830 that is like the one in FIG. 8-1 might lead to a conclusion in step 840 that the detected contaminants are less than 10 microns in size. Conversely, a histogram like the one in FIG. 8-2 might lead to a conclusion in step 845 that the detected contaminants are greater than 10 microns in size.

The thresholds used in steps 815 and 825 can be predetermined by experimentation. Step 835 could include computation of a statistic for the histogram constructed in step 830. For instance, in step 835 the process can calculate a standard deviation and then classify the distribution spread as either narrow or wide by comparing the calculated standard deviation to a predetermined threshold standard deviation. The process described with reference to FIGS. 8, 8-1, and 8-2 could be used alone or in combination with the processes described with reference to FIGS. 6, 7, and/or 9 to determine the size of contaminants.

FIG. 9 is a flow diagram of a contaminant type classification method, according to an embodiment of the invention. The process in FIG. 9 may be especially applicable where air or vapor could otherwise induce false positive results using other contaminant detection and classification methods. The illustrated process begins in step 905 by generating a pulse stream in a primary transducer. The pulse stream output from the primary transducer may be in response to a primary transmission signal Primary Tx. In step 910, the process receives a reflected signal from the primary transducer and the secondary transducer (i.e., the Primary Rx signal and Secondary Rx signal, respectively). The process calculates a primary channel power in step 913. Step 913 could include, for instance, calculating an average power/pulse in the Primary Rx signal and then aggregating the average power/pulse over a predetermined period of time. Then, in conditional step 915, the process determines whether individual contaminants are detected in the Primary Rx signal. Step 915 may include comparing the primary channel power to a predetermined threshold.

If the process does not detect contaminants (or a sufficient quantity of contaminants) in the Primary Rx signal, the process returns to step 905; otherwise the process determines in conditional step 920 whether the contaminants in Primary Rx signal are in phase with the primary transmission waveform (Primary Tx). If not, the process classifies the contaminant as air in step 935; otherwise, the process classifies the contaminants as non-air (e.g., water and/or particulate) in step 925.

Subsequent to step 925, the process tabulates contaminant detection in step 930. Tabulation step 930 includes logging the pulse number, measured power, and distance (and/or corresponding time-of-flight) for each pulse of the primary and secondary data (i.e., the Primary Rx signal and the Secondary Rx signal). Next, the process determines in conditional step 940 whether contaminants are detected in the Secondary Rx signal that correlate with contaminant detections in the Primary RX signal. A successful correlation in step 940 requires detections in the Primary Rx signal and Secondary Rx signal within a narrow distance (or time-of-flight) that corresponds to the crossing of the focused sound beams 330 and 335. If there is no correlation, the process returns to step 905; otherwise, the process calculates a secondary channel power in step 943 and divides the primary channel power by the secondary channel power to determine a classification ratio (CR) in step 945. Step 943 could include calculating an average power/pulse in the Secondary Rx signal and then aggregating the average power/pulse over a predetermined period of time.

In step 950, the process determines whether the CR is less than a predetermined lower threshold. Where conditional step 950 is satisfied, the process classifies the contaminant as particulate in step 955; otherwise, the process advances to conditional step 960. In conditional step 960, the process determines whether the CR is greater than a predetermined upper threshold. Where step 960 is satisfied, the process classifies the contaminant as water in step 965; otherwise, the process classifies the contaminants as having an unknown composition in step 970.

The thresholds used in steps 950 and 960 can be predetermined by experimentation.

Alternative System Embodiments

Figure 10:
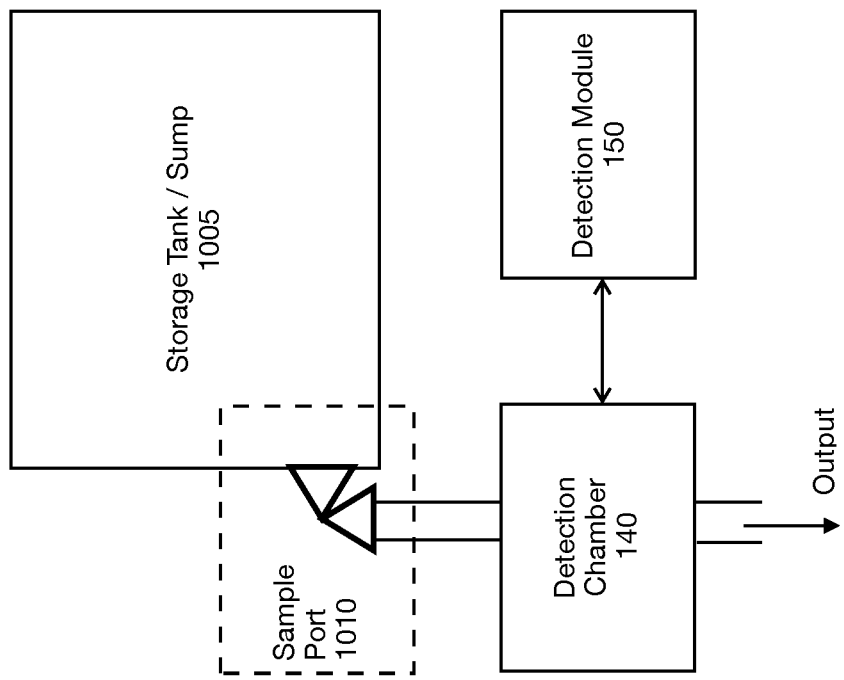
FIG. 10 is a functional block diagram of a contaminant detection and classification system, according to an embodiment of the invention.

FIG. 10 is a functional block diagram of a contaminant detection and classification system, according to an embodiment of the invention. As shown therein, a detection chamber 140 is connected to a storage tank/sump 1005 via a sample port 1010. A detection module 150 is electrically connected to the detection chamber 140. In operation, a sample of fluid drawn from the storage tank/sump 1005 and output from the detection chamber 140 is analyzed (e.g., as to composition and/or size of particulate contamination in the sample of fluid) by the detection module 150.

Figure 11:
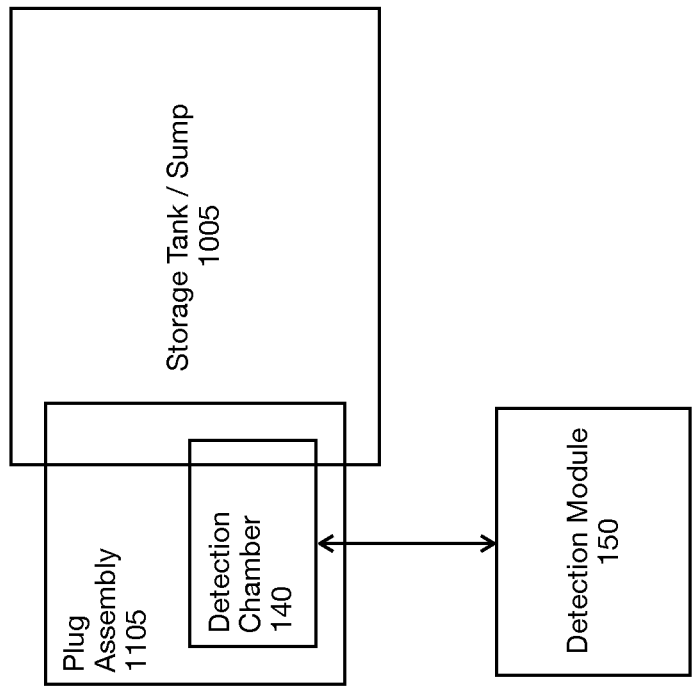
FIG. 11 is a functional block diagram of a contaminant detection and classification system, according to an embodiment of the invention.

FIG. 11 is a functional block diagram of a contaminant detection and classification system, according to an embodiment of the invention. In the illustrated embodiment, at least a portion of a detection chamber 140 is disposed in the storage tank/sump 1005 as part of a plug assembly 1105. A detection module 150 is electrically connected to the detection chamber 140. In operation, a fluid in the detection chamber 140 is analyzed (e.g., as to type and/or size of contamination in the fluid) by the detection module 150. In a variant of the illustrated embodiment, the detection module 150 is included in the plug assembly 1105.

Any one or more of the process described above with reference to FIGS. 6-9 could be implemented in the systems illustrated in FIGS. 1, 2, 10 and 11.

Summary

Embodiments of the invention thus provide improved systems and methods for detecting, measuring, classifying, and/or trapping contaminants in a fluid. The improved systems and methods can be configured to operate inline (bypass or full flow) or in a static tank environment. Advantageously, embodiments of the invention identify and measure both particulate and water content, can be tailored to identify contamination of a predetermined size or concentration, and can exclude air/vapor as a source of false alarms.

Those skilled in the art can readily recognize that numerous variations and substitutions may be made in the invention, its use and its configuration to achieve substantially the same results as achieved by the embodiments described herein. For example, the same or similar system and/or methods disclosed herein could be adopted for managing contamination in fluids other than fuel or oil. The quantity of test chambers and the operational frequencies of the test chambers could be varied according to application requirements. The functions of the detection module could be implemented in a variety of alternative technologies. Features disclosed in this specification could be combined in ways not expressly illustrated or discussed. Accordingly, there is no intention to limit the invention to the disclosed exemplary forms. Many variations, modifications and alternative constructions fall within the scope and spirit of the disclosed invention.

We claim:

1. A contaminant detection apparatus comprising:
   a detection chamber including
      a housing with an internal fluid conduit,
      a primary acoustic transducer, and
      a secondary acoustic transducer, the primary acoustic transducer and the secondary acoustic transducer being disposed in the housing such that a focal beam of the primary acoustic transducer and a focal beam of the secondary acoustic transducer intersect in the internal fluid conduit, the secondary acoustic transducer being disposed in the housing at an angle greater than 0 degrees and less than 180 degrees with respect to the primary acoustic transducer, and;

a detection module coupled to the primary acoustic transducer and the secondary acoustic transducer, the detection module configured to output a primary transmission (Primary Tx) signal to the primary acoustic transducer, the detection module configured to receive a primary reflected (Primary Rx) signal from the primary acoustic transducer and a secondary reflected (Secondary Rx) signal from the secondary acoustic transducer, the detection module further configured to detect a contaminant in a fluid contained in the internal fluid conduit based on the Primary Rx signal and the Secondary Rx signal, the detection module configured to:
  cause the primary acoustic transducer to output a pulse stream, the outputting being a response to the Primary Tx signal;
  receiving the Primary Rx signal from the primary acoustic transducer and the Secondary Rx signal from the secondary acoustic transducer in response to the pulse stream;
  filtering the Primary Rx signal and the Secondary Rx signal;
  calculating an average power/pulse in the Primary Rx signal;
  calculating a primary channel power based on the average power/ pulse in the Primary Rx signal for a predetermined period of time;
  calculating an average power/pulse in the Secondary Rx signal;
  calculating a secondary channel power based on the average power/pulse in the Secondary Rx signal for the predetermined period of time;
  dividing the primary channel power by the secondary channel power to calculate a classification ratio (CR);
  if the CR is less than a predetermined lower threshold, classifying the contaminant in the fluid as particulate;
  if the CR is greater than a predetermined upper threshold, classifying the contaminant in the fluid as water; and
  if the CR is not less than the predetermined lower threshold and not greater than the predetermined upper threshold, classifying the contaminant in the fluid as a mix of particulate and water.

2. The apparatus of claim 1, the process further including:
if the contaminant has been classified as particulate, determining a particulate concentration in the fluid based on the primary channel power;
if the contaminant has been classified as water, determining a water concentration in the fluid based on the primary channel power; and
if the contaminant has been classified as a mix of particulate and water, determining a particulate concentration and a water concentration in the fluid based on the primary channel power and the CR.

3. A contaminant detection apparatus comprising:
a detection chamber including
  a housing with an internal fluid conduit,
  a primary acoustic transducer, and
  a secondary acoustic transducer, the primary acoustic transducer and the secondary acoustic transducer being disposed in the housing such that a focal beam of the primary acoustic transducer and a focal beam of the secondary acoustic transducer intersect in the internal fluid conduit, the secondary acoustic transducer being disposed in the housing at an angle greater than 0 degrees and less than 180 degrees with respect to the primary acoustic transducer, and;

a detection module coupled to the primary acoustic transducer and the secondary acoustic transducer, the detection module configured to output a primary transmission (Primary Tx) signal to the primary acoustic transducer, the detection module configured to receive a primary reflected (Primary Rx) signal from the primary acoustic transducer and a secondary reflected (Secondary Rx) signal from the secondary acoustic transducer, the detection module further configured to detect a contaminant in a fluid contained in the internal fluid conduit based on the Primary Rx signal and the Secondary Rx signal, the detection module configured to:
  cause the primary transducer to output a pulse stream, the outputting being a response to the Primary Tx signal;
  receiving the Primary Rx signal from the primary acoustic transducer and the Secondary Rx signal from the secondary acoustic transducer in response to the pulse stream;
  calculating a primary channel power based on the Primary Rx signal;
  detecting a contaminant signature in the Primary Rx signal based on the primary channel power, and determining whether the contaminant signature in the Primary Rx signal is in phase with the Primary Tx signal;
  if the contaminant signature in the Primary Rx signal is not in phase with the Primary Tx signal, classifying the contaminant in the fluid as air;
  if the contaminant signature in the Primary Rx signal is in phase with the Primary Tx signal, determining a power and a distance for each pulse in the Primary Rx signal and the Secondary Rx signal;
  detecting a contaminant signature in the Secondary Rx signal, and determining whether the contaminant signature in the Secondary Rx signal correlates with the contaminant signature in the Primary Rx signal;
  if the contaminant signature in the Secondary Rx signal correlates with the contaminant signature in the Primary Rx signal, calculating a secondary channel power based on the Secondary Rx signal;
  dividing the primary channel power by the secondary signal channel power to determine a classification ratio (CR);
  if the CR is less than a predetermined lower threshold, classifying the contaminant in the fluid as particulate; and if the CR is greater than a predetermined upper threshold, classifying the contaminants contaminant in the fluid as water.

4. A method for detecting a contaminant in a fluid, the method comprising:
receiving a Primary Tx signal in a primary acoustic transducer;
outputting a pulse stream from the primary acoustic transducer in response to the Primary Tx signal;
receiving a Primary Rx signal from the primary acoustic transducer and a Secondary Rx signal from a secondary acoustic transducer in response to the pulse stream;
filtering the Primary Rx signal and the Secondary Rx signal;
calculating an average power/pulse in the Primary Rx signal;

calculating a primary channel power based on the average power/pulse in the Primary Rx signal for a predetermined period of time;
calculating an average power/pulse in the Secondary Rx signal;
calculating a secondary channel power based on the average power/pulse in the Secondary Rx signal for the predetermined period of time;
dividing the primary channel power by the secondary signal channel power to calculate a classification ratio (CR);
if the CR is less than a predetermined lower threshold, classifying the contaminant as particulate;
if the CR is greater than a predetermined upper threshold, classifying the contaminant as water; and
if the CR is not less than the predetermined lower threshold and not greater than the predetermined upper threshold, classifying the contaminant as a mix of particulate and water.

5. The method of claim 4 further comprising:
if the contaminant has been classified as particulate, determining a particulate concentration in the fluid based on the primary channel power;
if the contaminant has been classified as water, determining a water concentration in the fluid based on the primary channel power; and
if the contaminant has been classified as a mix of particulate and water, determining a particulate concentration and a water concentration in the fluid based on the primary channel power and the CR.

6. A method for detecting a contaminant in a fluid, the method comprising:
receiving a Primary Tx signal in a primary acoustic transducer;
outputting a pulse stream from the primary acoustic transducer in response to the Primary Tx signal;
receiving a Primary Rx signal from the primary acoustic transducer and a Secondary Rx signal from a secondary acoustic transducer in response to the pulse stream;
calculating a primary channel power based on the Primary Rx signal;
detecting a contaminant signature in the Primary Rx signal based on the primary channel power, and determining whether the contaminant signature in the Primary Rx signal is in phase with the Primary Tx signal;
if the contaminant signature in the Primary Rx signal is not in phase with the Primary Tx signal, classifying the contaminant in the fluid as air;
if the contaminant signature in the Primary Rx signal is in phase with the Primary Tx signal, determining a power and a distance for each pulse in the Primary Rx signal and the Secondary Rx signal;
detecting a contaminant signature in the Secondary Rx signal, and determining whether the contaminant signature in the Secondary Rx signal correlates with the contaminant signature in the Primary Rx signal;
if the contaminant signature in the Secondary Rx signal correlates with the contaminant signature in the Primary Rx signal, calculating a secondary channel power based on the Secondary Rx signal;
dividing the primary channel power by the secondary channel power to determine a classification ratio (CR);
if the CR is less than a predetermined lower threshold, classifying the contaminant in the fluid as particulate; and
if the CR is greater than a predetermined upper threshold, classifying the contaminant in the fluid as water.

* * * * *